US006890312B1

United States Patent
Priester et al.

(10) Patent No.: US 6,890,312 B1
(45) Date of Patent: May 10, 2005

(54) JOINT ANGLE INDICATION SYSTEM

(75) Inventors: William B. Priester, 8723 Windrush, Jackson, TN (US) 38125; Joseph H. Butler, Jr., Knoxville, TN (US); Michael J. Twigg, Knoxville, TN (US)

(73) Assignee: William B. Priester, Memphis, TN (US)

( * ) Notice: Subject to any disclaimer, the term of this patent is extended or adjusted under 35 U.S.C. 154(b) by 421 days.

(21) Appl. No.: 10/008,293

(22) Filed: Dec. 3, 2001

(51) Int. Cl.$^7$ .............................................. A61B 5/103
(52) U.S. Cl. ........................... 600/595; 33/512; 33/534
(58) Field of Search ................................ 600/587, 595; 33/511, 512, 1, 534

(56) References Cited

U.S. PATENT DOCUMENTS

| | | |
|---|---|---|
| 4,660,829 A | 4/1987 | Whiteneir |
| 4,667,685 A | 5/1987 | Fine |
| 5,027,688 A | 7/1991 | Suzuki et al. |
| 5,220,308 A | 6/1993 | Batzdorff et al. |
| 5,290,964 A | 3/1994 | Hiyoshi et al. |
| 5,324,038 A | 6/1994 | Sasser |
| 5,435,321 A | 7/1995 | McMillen et al. |
| 5,469,862 A | 11/1995 | Kovacevic |
| 5,474,088 A | 12/1995 | Zaharkin et al. |
| 5,509,809 A | 4/1996 | Clay |
| 5,586,943 A | 12/1996 | Clay |
| 5,704,846 A | 1/1998 | Johnson |
| 5,754,121 A | 5/1998 | Ward et al. |
| 5,792,077 A * | 8/1998 | Gomes ........................ 600/595 |
| 5,823,886 A | 10/1998 | Murray |
| 6,032,530 A * | 3/2000 | Hock ........................... 600/595 |
| 6,428,490 B1 * | 8/2002 | Kramer et al. ............... 600/595 |
| 2003/0088196 A1 * | 5/2003 | Burton ........................ 600/587 |

* cited by examiner

Primary Examiner—Max F. Hindenburg
Assistant Examiner—Jonathan Foreman
(74) Attorney, Agent, or Firm—Luedeka, Neely & Graham, P.C.

(57) ABSTRACT

A joint angle indication system provides information related to an angular relationship between a first body part and a second body part that are pivotally coupled at a joint. The system includes a first arm member attached to the first body part, and a second arm member attached to the second body part. One end of the second arm member is pivotally coupled to one end of the first arm member. The system includes one or more joint angle variation sensors that provide one or more electrical characteristics that vary based on variation in the joint angle between the first and second arm members. The joint angle is variable over an angular range that includes a first angle and a second angle. A biofeedback circuit generates a first feedback signal when the joint angle is less than or equal to the first angle, generates a second feedback signal when the joint angle is greater than or equal to the second angle, and generates no feedback signal when the joint angle is less than the second angle and greater than the first angle. Preferably, the first and second feedback signals are audio signals, and the second feedback signal has a different frequency from the first feedback signal. The system also includes an angle display circuit that is electrically coupled to the one or more joint angle variation sensors. The angle display circuit visually displays a joint angle value based on the one or more electrical characteristics.

24 Claims, 9 Drawing Sheets

JOINT ANGLE INDICATION SYSTEM

FIELD

This invention relates to the field of monitoring and providing feedback relative to body motion and posture. More particularly, the invention relates to a system for monitoring, indicating, and providing biofeedback relative to the angular orientation of one body part relative to another body part or relative to the trunk of the body.

BACKGROUND

In fields such as medicine and sports, it is often desirable to maintain a particular angular relationship between two body parts as they pivot about a joint during physical activity or as they relate to one another with regard to correct posture. For example, it is important to a right-handed golfer to maintain the proper angle between the left wrist and the left forearm while striking the ball on a drive. In orthopedic physical therapy, a patient is typically instructed to exercise a joint by moving one body part relative to another through a particular angular range. In everyday life, maintaining the proper angular relationship between the neck and the lower spine is critical in maintaining good posture.

Although devices have been developed for monitoring angular relationships between body parts and providing biofeedback, the prior devices have been inadequate for various reasons. Devices developed for use during sporting activities have been uncomfortable to wear and unwieldy to operate. Devices developed for medical use have been expensive, often due to the incorporation of data collection and analysis features that are rarely used.

What is needed, therefore, is an uncomplicated, inexpensive, comfortable, and easily operated joint angle indication system that is useful in sports training, posture training, and medical therapeutic settings.

SUMMARY

The above and other needs are met by a joint angle indication system which provides information related to an angular relationship between a first body part and a second body part that are pivotally coupled at a joint. The system includes a first arm member attached to the first body part, and a second arm member attached to the second body part. The first arm member has a first proximal end and a first distal end, and the second arm member has a second proximal end and a second distal end. The second proximal end of the second arm member is pivotally coupled to the first proximal end of the first arm member. The system also includes one or more joint angle variation sensors for providing one or more electrical characteristics which vary based on variation in a joint angle of the first arm member relative to the second arm member. The joint angle is variable over an angular range which includes a first angle and a second angle.

A biofeedback circuit is electrically coupled to the one or more joint angle variation sensors. The biofeedback circuit generates a first feedback signal when the one or more electrical characteristics indicate the joint angle is less than or equal to the first angle, generates a second feedback signal when the one or more electrical characteristics indicate the joint angle is greater than or equal to the second angle, and generates no feedback signal when the one or more electrical characteristics indicate the joint angle is less than the second angle and greater than the first angle.

In preferred embodiments, the first and second feedback signals are audio signals, where the first feedback signal is aurally different from the second feedback signal. In alternative embodiments, the first and second feedback signals may be visual signals, such as generated by two different-colored light emitting diodes, or vibration signals, such as generated by a vibrator unit operating at two different frequencies.

The system also includes an angle display circuit which is electrically coupled to the one or more joint angle variation sensors. The angle display circuit visually displays a joint angle value based on the one or more electrical characteristics.

In a most preferred embodiment, the one or more joint angle variation sensors include first and second potentiometers coupled between the first and second arm members, and the one or more electrical characteristics include a first electrical resistance of the first potentiometer and a second electrical resistance of the second potentiometer.

Also in a preferred embodiment, the first arm member is forked at the first proximal end to form a first prong portion and a second prong portion. The second proximal end of the second arm member is disposed between the first and second prong portions of the first arm member. The first potentiometer of this embodiment is disposed between the second arm member and the first prong of the first arm member, and the second potentiometer is disposed between the second arm member and the second prong of the first arm member.

Some preferred embodiments include an audio output circuit that is electrically coupled to the one or more joint angle variation sensors. The audio output circuit generates an audio angle indication signal having a signal characteristic, such as frequency or amplitude, which varies in relation to a variation in the one or more electrical characteristics provided by the one or more joint angle variation sensors. Some preferred embodiments also include a microphone for generating an audio annotation signal. An audio recording device, such as a portable audio cassette tape recorder, may be used to record the audio angle indication signal on a first audio channel and the audio annotation signal on a second audio channel.

In another aspect, the invention provides a method for providing information related to an angular relationship between first and second body parts coupled at a joint. The method includes providing at least one electrical characteristic which varies based on variation in a joint angle of the first body part relative to the second body part. The method also includes generating an audio angle indication signal having a signal characteristic, such as frequency or amplitude, which varies in relation to a variation in the at least one electrical characteristic, and generating an audio annotation signal. The audio angle indication signal is recorded on a first audio information channel of an audio recording device, and the audio annotation signal is recorded on a second audio information channel of the audio recording device. The audio angle indication signal is accessed from the first audio information channel of the audio recording device, and the audio annotation signal is accessed from the second audio information channel of the audio recording device. The audio angle indication signal is operated on to derive a joint angle value therefrom. The joint angle value is visually displayed on a display device while an audible rendition of the audio annotation signal is provided.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
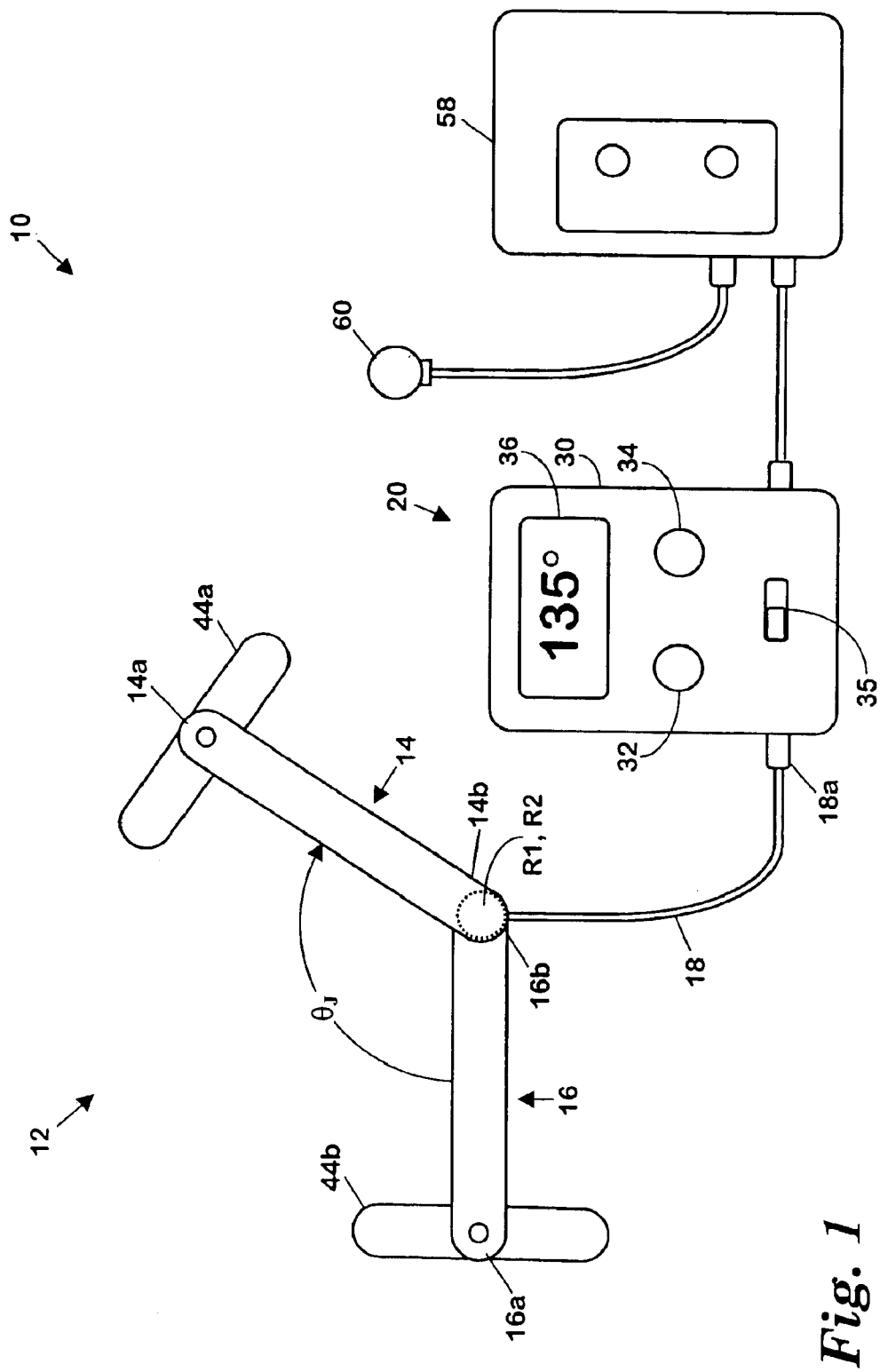
FIG. 1 depicts a joint angle indication system according to a preferred embodiment of the invention.
Figure 2:
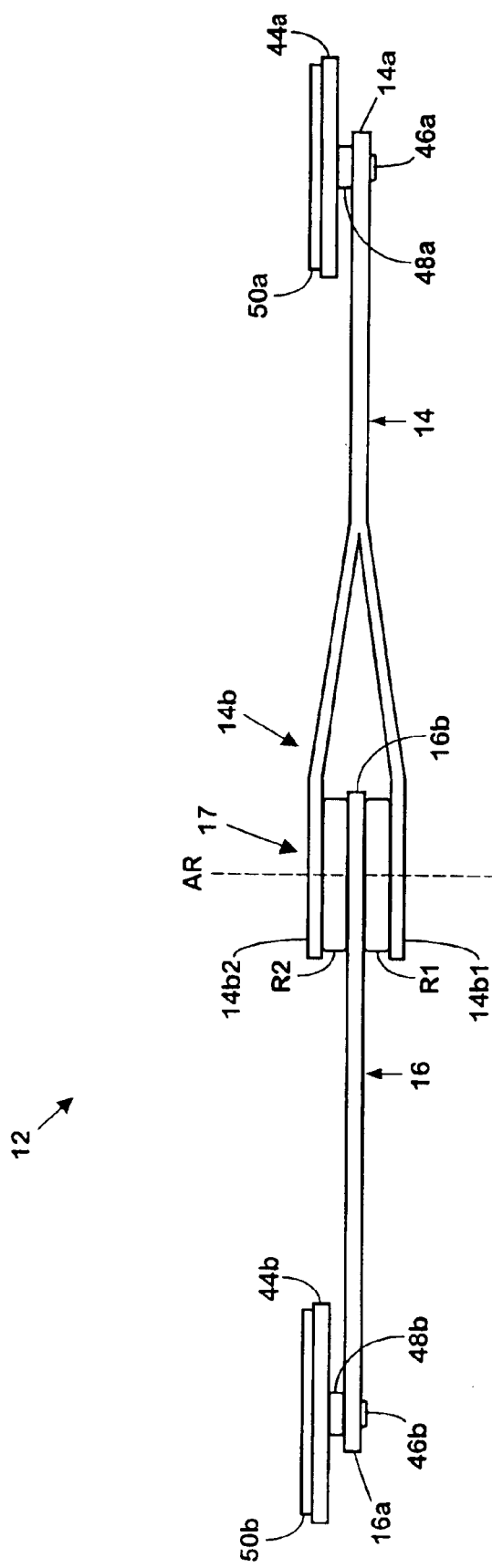
FIG. 2 depicts an angle sensing structure according to a preferred embodiment of the invention.
Figure 3:
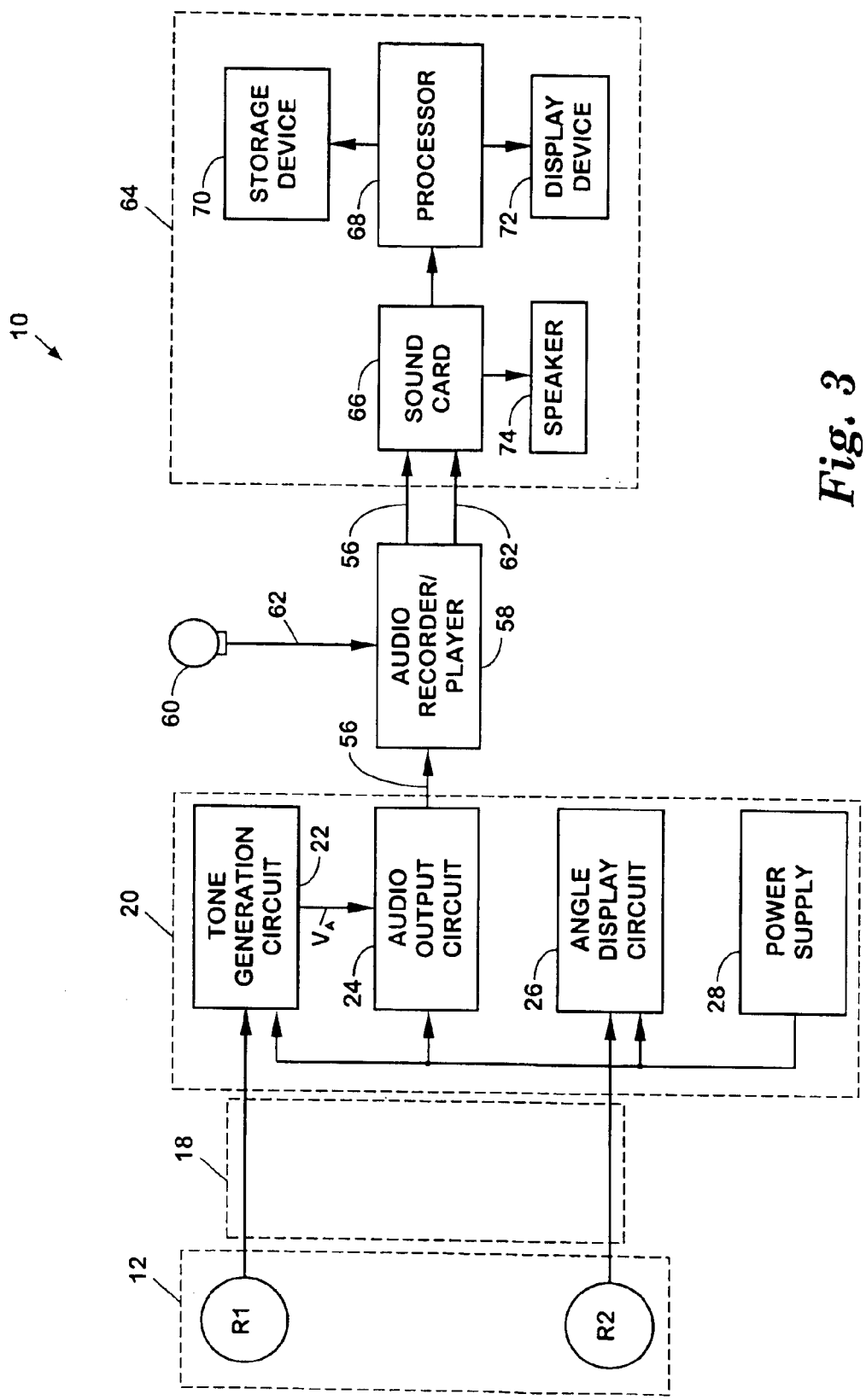
FIG. 3 is a functional block diagram of a joint angle indication system according to a preferred embodiment of the invention.

Referring now to FIGS. 1, 2, and 3, there is generally depicted a preferred embodiment of a joint angle indication system 10. The system 10 includes an angle sensing structure 12 having a first arm member 14 and a second arm member 16. The first arm member 14 has a distal end 14a and a proximal end 14b, and the second arm member 16 has a distal end 16a and a proximal end 16b. Preferably, the arm members 14 and 16 are formed of a semi-rigid material, such as an injection-moldable thermoplastic, but could also be formed of aluminum or other metals, or a composite material.

The arm members 14 and 16 are preferably somewhat flexible in a direction normal to the plane containing the joint angle $\theta_J$. This preferred flexibility accommodates out-of-plane bending of a joint such as the wrist, which may flex not only up and down, but also side to side. Thus, the preferred embodiment of the angle sensing structure 12 allows measurement, for example, of the up and down motion of the wrist, while still permitting side to side rotation.

As shown in FIGS. 1 and 2, the proximal ends 14b and 16b of the first and second arm members 14 and 16 are pivotally coupled, so that the first arm member 14 may rotate in relation to the second arm member 16. The angular relationship between the first and second arm members 14 and 16 is defined by the joint angle $\theta_J$.

Figure 6A:
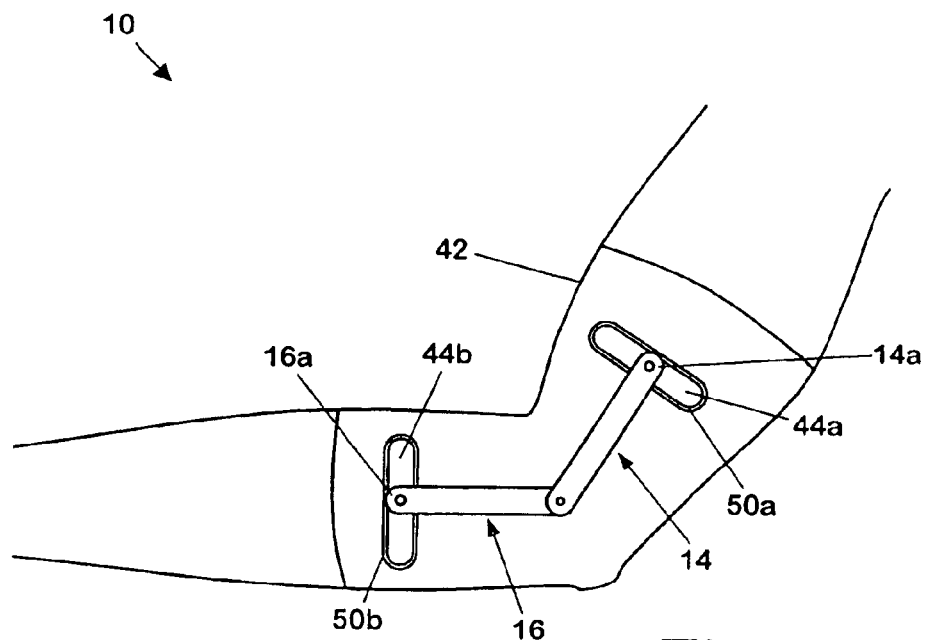
FIG. 6A depicts an angle sensing structure attached to the arm of a wearer according to a preferred embodiment of the invention.
Figure 6B:
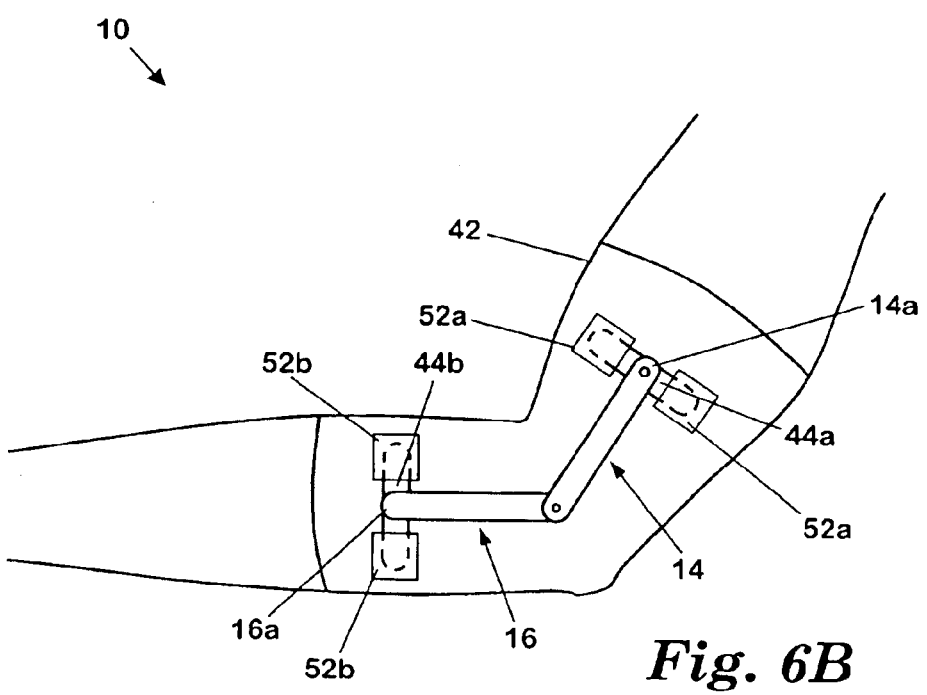
FIG. 6B depicts an angle sensing structure attached to the arm of a wearer according to an alternative embodiment of the invention.

In the preferred embodiment of the invention, the angle sensing structure 12 includes means for attaching the first and second arm members 14 and 16 to two adjacent body parts of a wearer. For example, as depicted in FIGS. 6A and 6B, the first arm member 14 may attach to the wearer's upper arm and the second arm member 16 may attach to the wearer's forearm. Preferably, when attached, the first arm member 14 is aligned substantially in parallel with the wearer's upper arm, the second arm member 16 is aligned substantially in parallel with the wearer's forearm, and the rotational axis AR (FIG. 2) of the first arm member 14 relative to the second arm member 16 is positioned so as to substantially coincide with the rotational axis of the wearer's elbow. In this manner, as the wearer's elbow bends, the joint angle $\theta_J$ changes correspondingly. Various means for attaching the first and second arm members 14 and 16 to the limbs of the wearer are described in more detail below.

Figure 7:
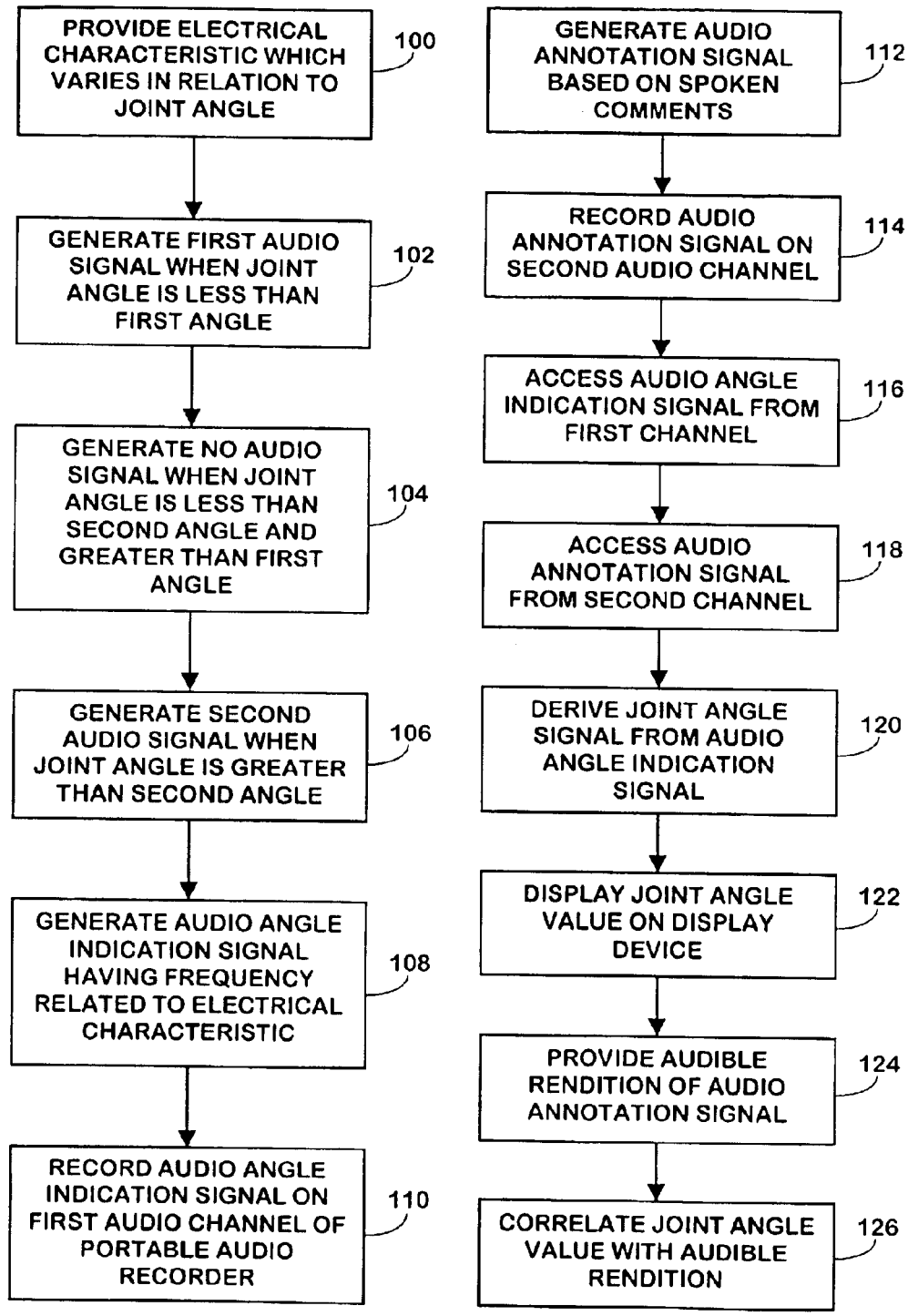
FIG. 7 depicts a functional flow diagram of a method for providing joint angle information according to a preferred embodiment of the invention.

As depicted in FIG. 2, one or more joint angle variation sensors 17, such as potentiometers R1 and R2, are disposed between the proximal ends 14b and 16b of the first and second arm members 14 and 16. The joint angle variation sensors 17 preferably provide an electrical characteristic which varies in relation to the variation in joint angle $\theta_J$ (step 100 in FIG. 7). For example, in the case of potentiometers R1 and R2, the electrical characteristic which varies in relation to the variation in joint angle $\theta_J$ is the electrical resistance at a center contact of the potentiometers R1 and R2. Preferably, the potentiometers R1 and R2 are of a type having a semicircular resistance element with electrical contacts at each end thereof, and a rotatable wiper element which contacts the resistance element. The rotatable wiper elements of the potentiometers R1 and R2 are preferably fixed in relation to the first arm member 14, and the semicircular resistance elements are fixed in relation to the second arm member 16. Alternatively, the rotatable wiper elements are fixed in relation to the second arm member 16, and the semicircular resistance elements are fixed in relation to the first arm member 14. In either case, as the first arm member 14 rotates in relation to the second arm member 16, the wiper elements rotate in relation to the semicircular resistance elements. Thus, as described in more detail hereinafter, the potentiometers R1 and R2 provide a variable voltage division network, where the voltage division varies with the rotation of the first arm member 14 in relation to the second arm member 16.

In a preferred embodiment, the proximal end 14b of the first arm member 14 is bifurcated, thereby providing first and second prong sections 14b1 and 14b2. As depicted in FIG. 2, the first potentiometer R1 is preferably disposed between the first prong section 14b1 and the proximal end 16b of the second arm member 16, and the second potentiometer R2 is disposed between the proximal end 16b and the second prong section 14b2. This novel arrangement provides a structurally sturdy joint, while also providing the desired rotational relationship between the wiper elements and resistance elements of the potentiometers R1 and R2.

As shown in FIG. 1, electrical connection to the potentiometers R1 and R2 is preferably provided by a flexible harness 18. In a preferred embodiment, the harness 18 includes a connector 18a for coupling the conductors of the harness 18 to an angle indication unit 20. The angle indication unit 20 is preferably housed within an impact-resistance thermoplastic housing 30. On the housing are a pair of controls 32 and 34 for setting an angular indication range. As described in more detail below, the control 32 is used to adjust a lower angle indication limit and the control 34 is used to adjust an upper angle indication limit. A display window 36 is provided in the housing 30 for visually indicating the angle $\theta_J$ in a numerical format. The unit 20 preferably includes a power switch 35 for turning the unit 20 on or off.

It will be appreciated that the electrical connection between the angle sensing unit 12 and the angle indication unit 20 could be accomplished by means other than a hard-wired connection as provided by the harness 18. For example, the angle sensing unit 12 may include a wireless transmitter for transmitting wireless signals related to the voltages on the potentiometers R1 and R2, and the angle indication unit 20 may include a wireless receiver for receiving such wireless signals. Thus, it should be appreciated that the invention is not limited to any particular means for providing electrical communication between the angle sensing unit 12 and the angle indication unit 20.

As depicted in FIG. 3, various functional components of the angle indication unit 20 include a biofeedback circuit 22, an audio output circuit 24, an angle display circuit 26, and a power supply 28. Preferably, the biofeedback circuit 22 is coupled via the harness 18 to the potentiometer R1. As described below, the biofeedback circuit 22 generates a first or low-frequency audible tone when the angle $\theta_J$ is less than a predetermined lower angular limit $\theta_{Jmin}$ (step 102 in FIG. 7), generates a second or high-frequency audible tone when the angle $\theta_J$ is greater than a predetermined upper angular limit $\theta_{Jmax}$ (step 106), and generates no tone when the angle $\theta_J$ is between the lower angular limit $\theta_{Jmin}$ and the upper angular limit $\theta_{Jmax}$ (step 104).

Figure 4:
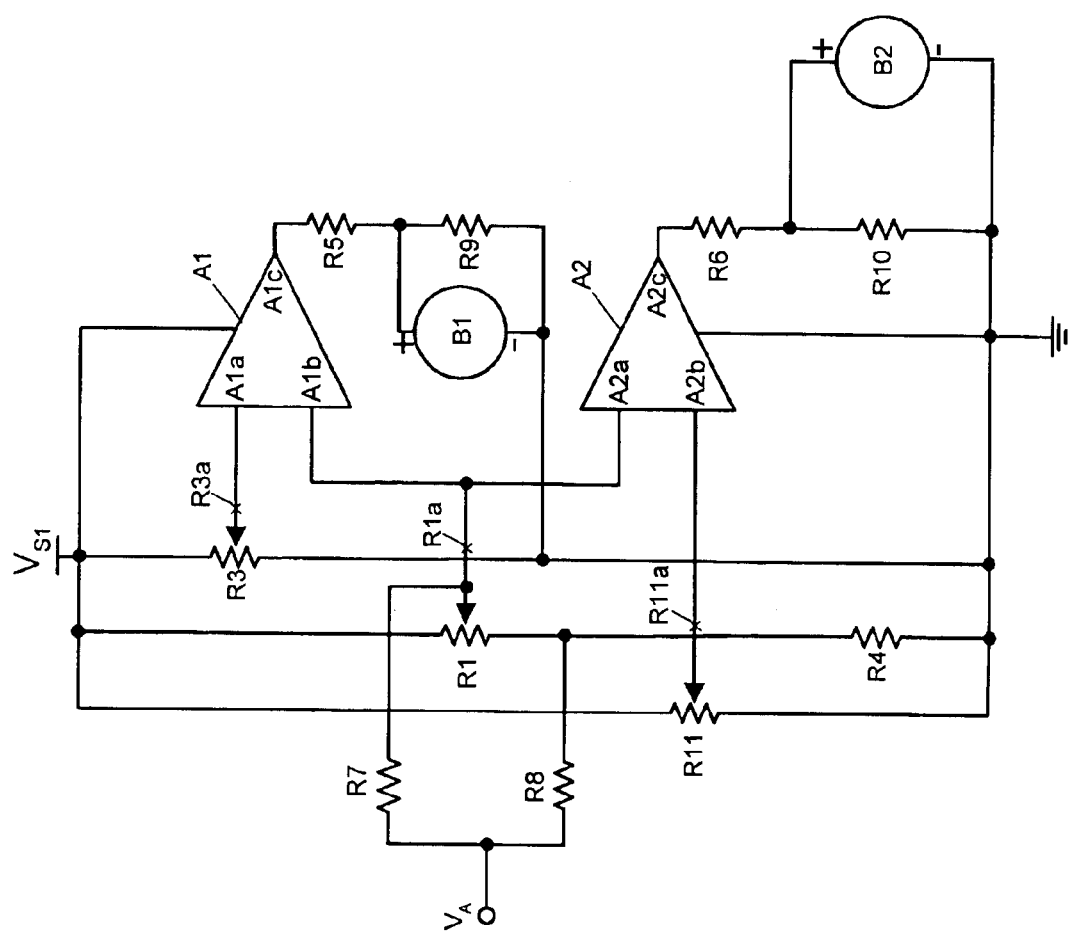
FIG. 4 is a schematic diagram of a biofeedback circuit according to a preferred embodiment of the invention.

A schematic diagram of one preferred embodiment of the biofeedback circuit 22 is depicted in FIG. 4. It should be appreciated that the circuit depicted in FIG. 4 provides one way to generate the low and high tones to indicate angle limits. However, one skilled in the art may conceive of other circuit configurations which provide this function. Thus, the invention is not limited to any particular configuration of the biofeedback circuit 22. As shown in FIG. 4, the potentiometer R1 and a resistor R4 form a voltage divider network, where the voltage on the circuit node R1a is provided to an input A1b of an operational amplifier A1 and to an input A2a of an operational amplifier A2. The potentiometer R3 forms another voltage divider, where the voltage on the circuit node R3a is provided to an input A1a of the operational amplifier A1. The potentiometer R11 forms yet another voltage divider, where the voltage on the circuit node R11a is provided to an input A2b of the operational amplifier A2.

Preferably, the voltage at the node R3a of the potentiometer R3 is used to set the lower angular limit of the biofeedback circuit 22, where the pot R3 is adjusted using the control 32 (FIG. 1). When the voltage on the node R1a is greater than the voltage on the node R3a, the output A1c of the operational amplifier A1 goes high. When the voltage at output A1c goes high, the voltage across the resistor R9 is sufficient to activate a piezoelectric buzzer B1. In the preferred embodiment, the buzzer B1 generates the first or low-frequency audible tone, such as a tone having a frequency of about 3000 HZ. Thus, as the joint angle $\theta_J$ decreases to a value less than the lower angular limit $\theta_{Jmin}$, the voltage on the node R1a correspondingly decreases to a value less than the voltage on the node R3a, thereby causing the buzzer B1 to produce the low-frequency audible tone.

Similarly, the voltage at the node R11a of the potentiometer R11 is used to set the upper angular limit of the biofeedback circuit 22, where the pot R11 is adjusted using the control 34 (FIG. 1). When the voltage on the node R1a is less than the voltage on the node R11a, the output A2c of the operational amplifier A2 goes high. When the voltage at output A2c goes high, the voltage across the resistor R10 is sufficient to activate a piezoelectric buzzer B2. In the preferred embodiment, the buzzer B2 generates the second or high-frequency audible tone, such as a tone having a frequency of about 4000 HZ. Thus, as the joint angle $\theta_J$ increases to a value greater than the upper angular limit $\theta_{Jmax}$, the voltage on the node R1a correspondingly increases to a value greater than the voltage on the node R11a, thereby causing the buzzer B2 to produce the high-frequency audible tone.

As shown in FIG. 4, the biofeedback circuit 22 provides a voltage signal $V_A$ which varies in relation with the variation in the voltage on the node R1a. As described in more detail below, the voltage signal $V_A$ is provided to the audio output circuit 24 (See FIGS. 3 and 8).

Various suggested values for the resistor and capacitor circuit components of a preferred embodiment of the invention, including those of the biofeedback circuit 22, are listed in Table I.

TABLE I

| Component | Value |
|---|---|
| R1 | 50 KΩ |
| R2 | 50 KΩ |
| R3 | 50 KΩ |
| R4 | 22 KΩ |
| R5 | 2.2 KΩ |
| R6 | 2.2 KΩ |
| R7 | 2.2 KΩ |
| R8 | 100 Ω |
| R9 | 1 KΩ |
| R10 | 1 KΩ |
| R11 | 50 KΩ |
| R12 | 100 KΩ |
| R13 | 220 KΩ |
| R14 | 1 MΩ |
| R15 | 1 MΩ |
| R16 | 100 KΩ |
| R17 | 47 KΩ |
| R18 | 100 KΩ |
| R20 | 100 KΩ |
| R19 | 100 KΩ |
| R21 | 1.2 MΩ |
| R22 | 100 KΩ |
| R23 | 47 KΩ |
| R24 | 100 KΩ |
| R25 | 13 Ω |
| R26 | 10 KΩ |
| R27 | 6.8 KΩ |
| C1 | 10 nF |
| C2 | 470 nF |
| C3 | 220 nF |
| C4 | 100 nF |
| C5 | 100 pF |
| C6 | 0.1 µF |
| C7 | 1 µF |
| C8 | 0.01 µF |

Figure 5:
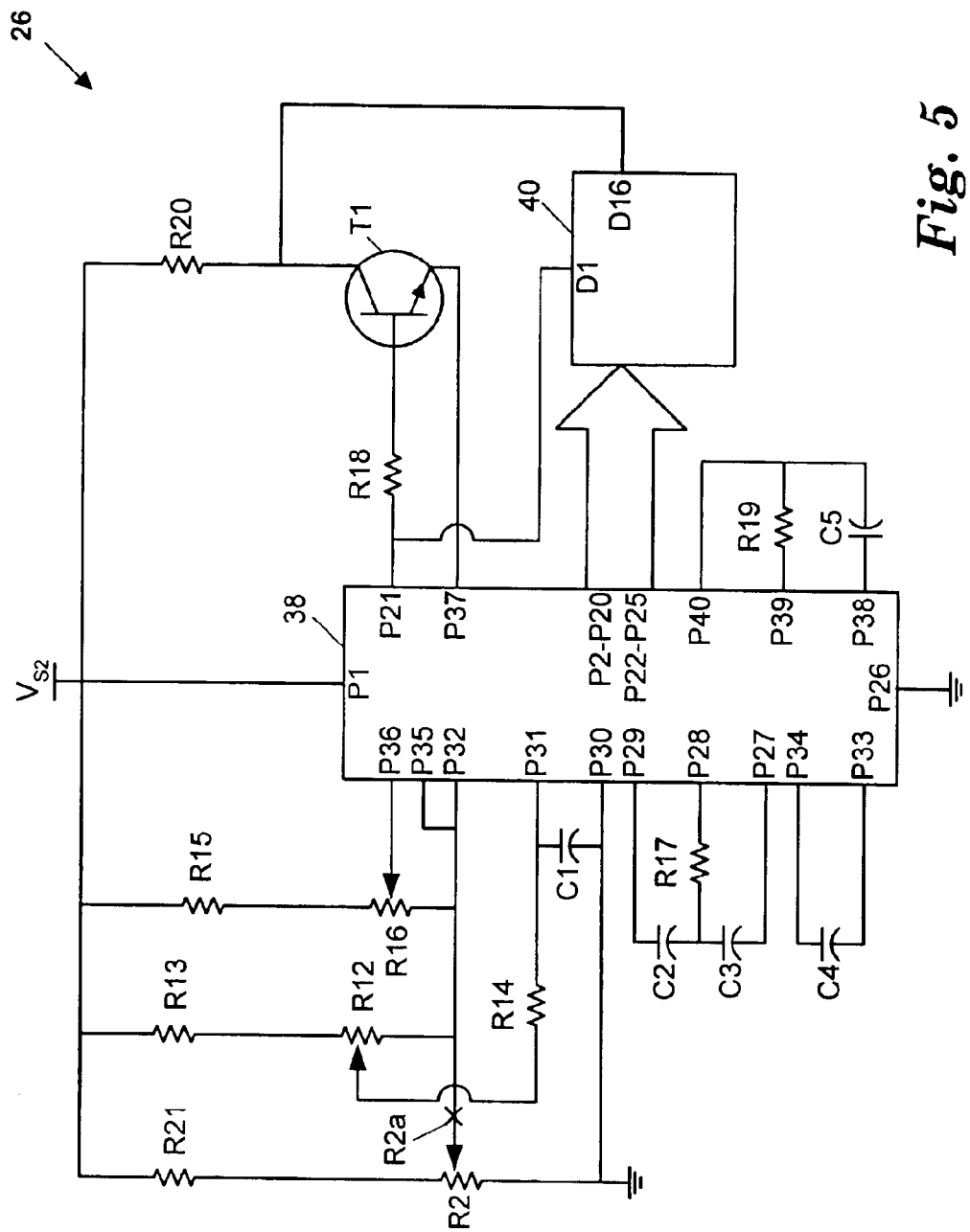
FIG. 5 is a schematic diagram of an angle display circuit according to a preferred embodiment of the invention.

Referring now to FIG. 5, a preferred embodiment of the angle display circuit 26 is depicted. As shown in FIG. 5, the circuit 26 includes an LCD driver circuit 38, such as an integrated circuit device having model number ICL7106 manufactured by Telecom Semiconductor, for driving a display device 40, such as a liquid crystal display (LCD) having model number VI-302-DP manufactured by Varitronix. The potentiometer R2 and a resistor R21 form a voltage divider network, where the voltage on the circuit node R2a is provided to input pins P32 and P35 of the LCD driver circuit 38. Preferably, as the position of the wiper contact of the potentiometer R2 varies from one extreme to another, the voltage on the node R2a varies from about 0.0 to 0.2 volts. The LCD driver circuit 38 translates this variation in voltage at node R2a into a set of signals on the pins P2–P20 and P22–P25 which are coupled to corresponding pins on the LCD display 40. Table II lists the corresponding pin connections for the LCD driver circuit 38 and the LCD display 40 of the preferred embodiment.

TABLE II

| Driver Circuit Pin | LCD Display Pin |
| --- | --- |
| P2 | D18 |
| P3 | D19 |
| P4 | D20 |
| P5 | D21 |
| P6 | D22 |
| P7 | D23 |
| P8 | D17 |
| P9 | D14 |
| P10 | D15 |
| P11 | D24 |
| P12 | D25 |
| P13 | D26 |
| P14 | D13 |
| P15 | D10 |
| P16 | D29 |
| P17 | D31 |
| P18 | D9 |
| P19 | D3 |
| P20 | D2 |
| P22 | 32 |
| P23 | 30 |
| P24 | 11 |
| P25 | 27 |

The potentiometers R12 and R16 are used to calibrate the angle display circuit by providing zero adjustment and gain adjustment, respectively, of the voltage on the node R2a. In the preferred embodiment, calibration is accomplished by positioning the first and second arm members 14 and 16 such that the joint angle $\theta_J$ is substantially zero degrees, and then adjusting the potentiometer R12 until a zero reading is displayed on the LCD display 40. The first and second arm members 14 and 16 are then positioned such that the joint angle $\theta_J$ set to a known angle, such as ninety degrees, and the potentiometer R14 is adjusted until the display corresponds to the known angle.

Although the preferred embodiments described above incorporate two potentiometers R1 and R2 for angle sensing, one skilled in the art will appreciate that a single potentiometer could be used instead. Any minor modifications to the circuits described above to accommodate the use of a single potentiometer in place of potentiometers R1 and R2 is well within the knowledge of one skilled in the art. Thus, it should be appreciated that the scope of the present invention is not limited to any particular number of potentiometers used in sensing the angular relationship between the first and second arm members 14 and 16.

Figure 8:
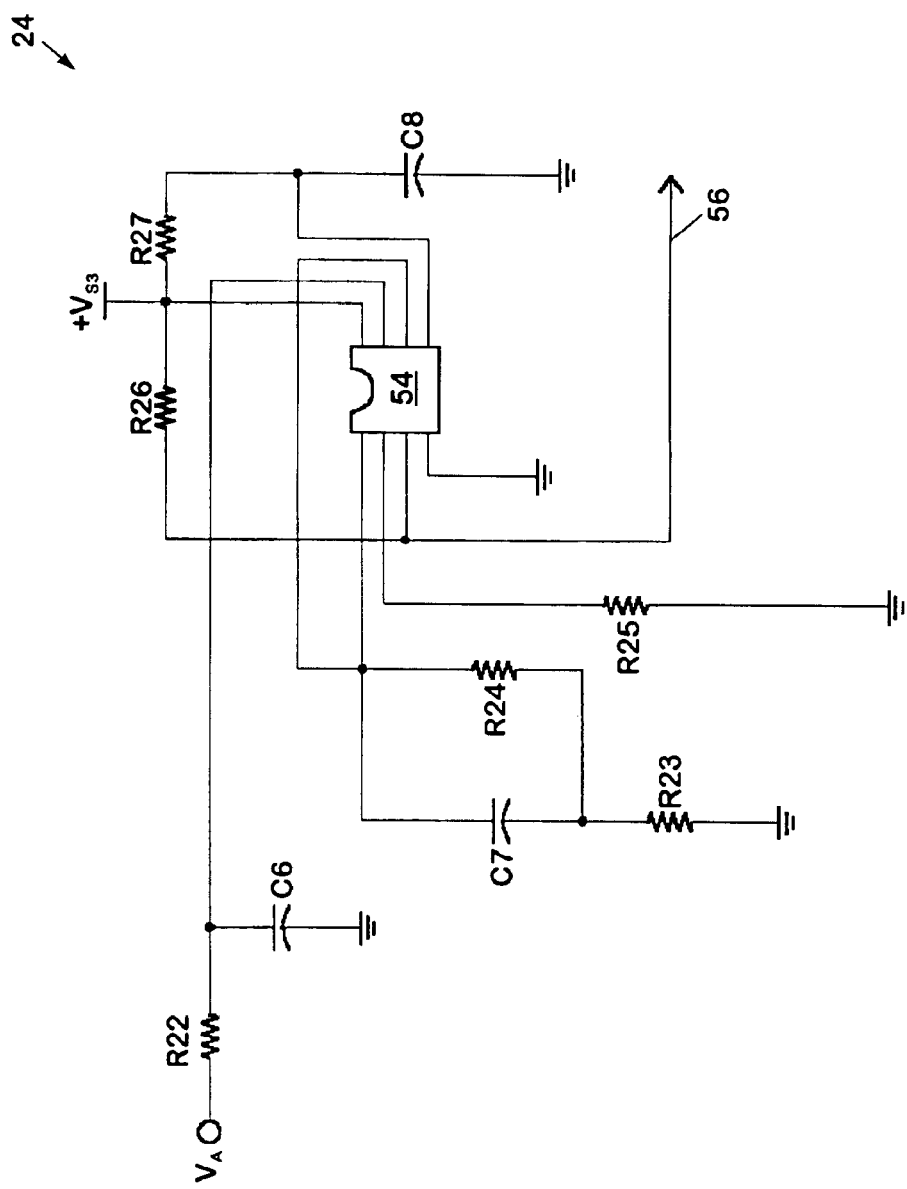
FIG. 8 is a schematic diagram of an audio output circuit according to a preferred embodiment of the invention.

In the preferred embodiment of the invention, the power supply 28 comprises one or more batteries, such a 9 volt battery, coupled to a power conditioning circuit. The power supply 28 provides power to the audio output circuit 24, the voltage $V_{S1}$, to the biofeedback circuit 22 (FIG. 4), the voltage $V_{S2}$ to the angle display circuit 26 (FIG. 5), and the voltages $+V_{S3}$ and $-V_{S3}$ to the audio output circuit 24 (FIG. 8).

FIGS. 6A and 6B depict two different ways to attach the angle sensing structure 12 to the wearer's arm. Both embodiments include first and second attachment plates 44a and 44b, which are preferably formed of a material similar to that of the first and second arm members 14 and 16, such as plastic or aluminum. As shown in FIG. 2, the first and second attachment plates 44a and 44b are pivotally attached to the first and second arm members 14 and 16, respectively, such as by pins 46a and 46b. Preferably, spacers 48a and 48b are provided between the first and second attachment plates 44a and 44b and the first and second arm members 14 and 16 to provide for free rotation of the first and second attachment plates 44a and 44b relative to the first and second arm members 14 and 16.

In preferred embodiments of the invention, the first and second attachment plates 44a and 44b are secured to the first and second body parts of the wearer in a manner which allows rotation of the first and second attachment plates 44a and 44b relative to the first and second arm members 14 and 16. In this manner, as the wearer flexes the joint, not only does the first arm member 14 rotate in relation to the second arm member 16, but the first arm member 14 is free to rotate in relation to the first attachment plate 44a, and the second arm member 16 is free to rotate in relation to the second attachment plate 44b. This feature, in conjunction with the preferred flexibility of the arm members 14 and 16, eliminates binding of the first arm member 14 relative to the second arm member 16, such as may occur when the axis of rotation AR of the angle sensing structure 12 (FIG. 2) is not perfectly aligned with the axis of rotation of the joint. Such binding has plagued prior angle measurement devices. By eliminating this sort of binding, the present invention provides a more accurate angle measurement, and reduces stress in the mechanical structure which could lead to mechanical failure.

As shown in FIGS. 6A and 6B, the system 10 preferably includes a flexible sleeve 42, made of a material such as neoprene, which surrounds the limb of the wearer. In the preferred embodiment, the sleeve 42 is similar in construction to an orthopedic brace, such as may be worn to provide support to a joint while allowing relatively unimpeded movement of the joint. Although the sleeve 42 depicted in FIGS. 6A and 6B is designed for use on the elbow, it will be appreciated that a similar sleeve 42 may be provided for the knee, wrist, or other joints to be monitored. Thus, the word sleeve as used herein encompasses a glove, sock, trunk girdle, harness, or any other type of device which provides for attaching the angle sensing structure to the body of the wearer. It should also be appreciated that the angle sensing structure 12 and attachment structures described herein are applicable for use on sleeves 42 configured for practically any joint on the body, and that modifications of the structures depicted in FIGS. 6A and 6B which may be required to accommodate other joint geometry's are well within the scope of the present invention.

Although FIGS. 6A and 6B depict the angle sensing structure 12 as being exposed on an outer surface of the sleeve 42, it should be appreciated that the structure 12 may also be completely enclosed within the material of the sleeve 42. In this manner, the angle sensing structure 12 may be protected from the elements, thereby allowing use of the device 10 while swimming or participating in other water-based activities.

FIGS. 6A and 6B depict two possible ways to secure the angle sensing structure 12 to the sleeve 42. As shown in FIGS. 6A and 2, a hook-and-fastener system 50a and 50b, such as VELCRO™, is provided between the first and second attachment plates 44a and 44b and the sleeve 42. In the embodiment of FIG. 6B, the ends of the first and second attachment plates 44a and 44b are captured within pairs of opposing pockets 52a and 52b attached to the sleeve 42. Alternatively, the ends of the attachment plates 44a and 44b may be captured within a pair of opposing slits in the material of the sleeve 42. One skilled in the art will appreciate that other fastening means may be used to couple the attachment plates 44a and 44b to the sleeve 42, such as snaps, and that any of those means are included within the scope of the invention. Regardless of the fastening means, the first and second attachment plates 44a and 44b are preferably securely attached to the sleeve, while the first and second arm members 14 and 16 are preferably free to rotate in relation to the first and second attachment plates 44a and 44b to prevent binding as the joint is flexed.

With reference again to FIGS. 1 and 3, a preferred embodiment of the system 10 is described which provides for recording joint angle information for later analysis. As shown in FIG. 3, the audio output circuit 24 is electrically coupled to the potentiometer R1. As the joint angle $\theta_J$ changes, as indicated by the change in resistance at the wiper contact of the potentiometer R1, the audio output circuit 24 generates an audio signal 56 which continuously varies in relation to the variations in angle $\theta_J$ (step 108 in FIG. 7). In the preferred embodiment, the audio signal 56, also referred to herein as the audio angle indication signal, is a sinusoidal signal having a constant amplitude, and having a frequency which varies within the audio frequency range in relation to variations in the joint angle $\theta_J$. In an alternative embodiment, the signal 56 has a constant frequency, but has an amplitude which varies in relation to variations in the joint angle $\theta_J$.

A schematic diagram of one preferred embodiment of the audio output circuit 24 is depicted in FIG. 8. It should be appreciated that the circuit depicted in FIG. 8 provides one way to generate the audio angle indication signal. However, one skilled in the art may conceive of other circuit configurations which provide this function. Thus, the invention is not limited to any particular configuration of the audio output circuit 24. Suggested values for the various circuit components of the audio output circuit 24 are listed in Table I.

Figure 9:
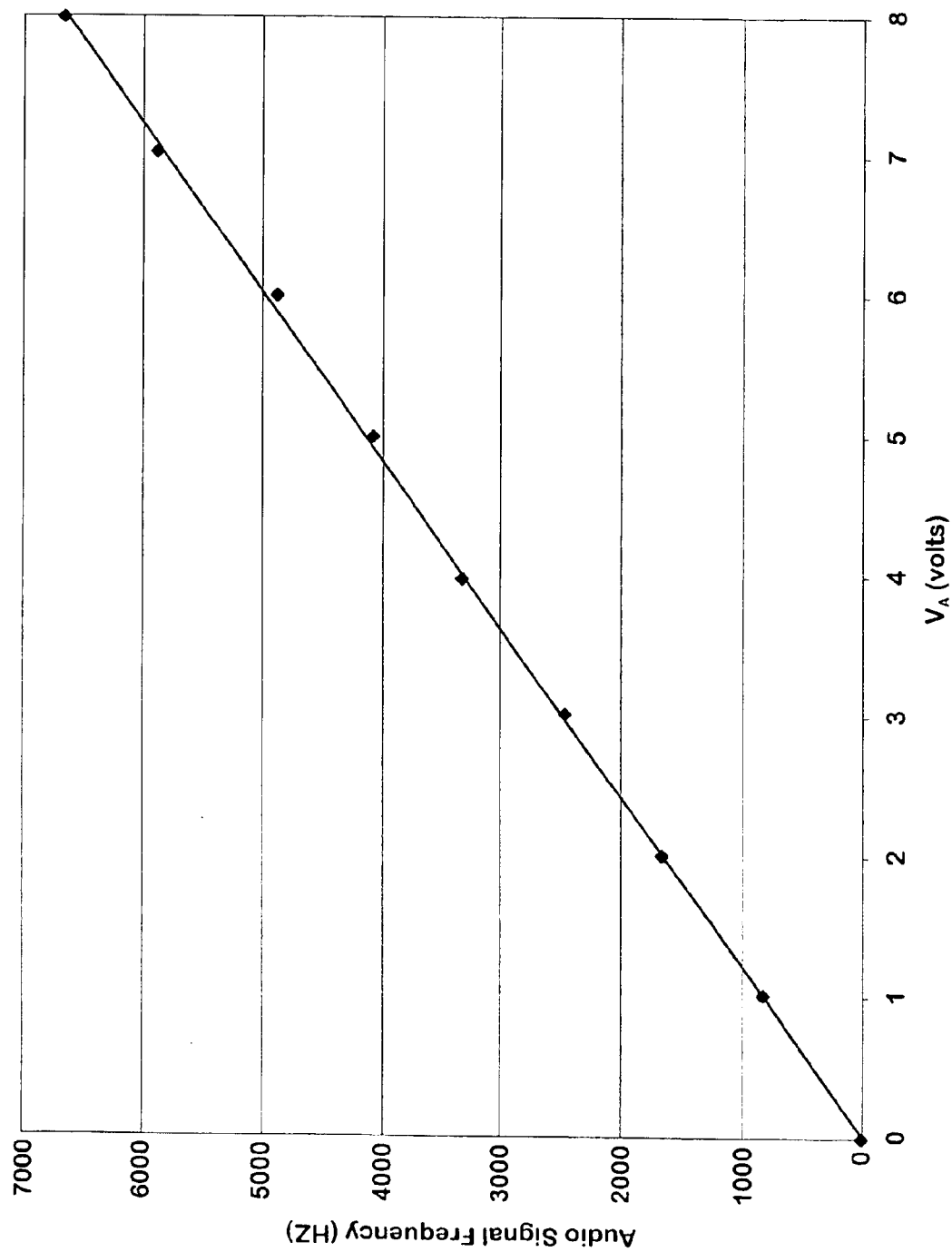
FIG. 9 depicts a voltage-to-frequency function provided by the audio output circuit of the preferred embodiment of the invention.

In the embodiment of FIG. 8, the audio output circuit 24 incorporates a voltage-to-frequency converter 54, such as an integrated circuit device having model number LM231/LM331 manufactured by National Semiconductor. Based on the voltage signal VA from the biofeedback circuit 22 (FIG. 4), the voltage-to-frequency converter 54 generates the audio signal 56. FIG. 9 depicts an example of the voltage-to-frequency function provided by the preferred embodiment of the converter 54.

As shown in FIG. 3, the audio signal 56 is provided to a first input channel, such as the left channel, of a two-channel audio record/playback device 58. The record/playback device 58 may be a portable analog stereo cassette tape player/recorder or a portable digital audio record/playback device. As the wearer performs various activities over a period of time, the audio angle indication signal 56 is recorded on the record/playback device 58 (step 110). In this manner, variations over time in the amplitude (or frequency) of the signal 56 in relation to variations in the joint angle $\theta_J$ are recorded by the record/playback device 58. As described in more detail below, the recorded variations in the signal 56 may be replayed and analyzed to determine the corresponding variations in the joint angle $\theta_J$ over time.

As depicted in FIGS. 1 and 3, the system 10 preferably includes a microphone 60 for generating an audio signal 62, also referred to herein as an audio annotation signal (step 112). Preferably, the audio annotation signal 62 is provided to a second input channel, such as the right channel, of the two-channel audio record/playback device 58 (step 114). In the preferred embodiment, the wearer of the angle sensing structure 12 may use the microphone 60 for recording voice annotations that are synchronous with the recording of the angle signal 56. These voice annotations may be used to provide an indication of what activities the wearer is performing at any particular time during the recording sequence. For example, as the wearer starts the motion of serving a tennis ball, the wearer may say, "Serving now".

Using the audio record/playback device 58, the audio angle indication signal 56 and the audio annotation signal 62 are simultaneously recorded on two channels of a recording medium, such as an audio cassette tape or a digital memory device. Using the same or another record/playback device 58, the signal 56 is accessed from the first channel of the recording medium (step 116), and the signal 62 is accessed from the second channel of the recording medium (step 118).

As depicted in FIG. 3, the signals 56 and 62 are provided to a joint angle analysis system 64. Preferably, the joint angle analysis system 64 is a personal computing device, such as desktop or laptop personal computer. In the preferred embodiment, the system 64 includes an audio interface, such as a sound card 66, coupled to a processor 68, a data storage device 70, a video display device 72, and one or more speakers or earphones 74 coupled to the sound card 66. The sound card 66 receives the first and second analog audio channels from the audio record/playback device 58, converts the analog signals 56 and 62 into digital signals, and provides the digital signals to the processor 68. Running on the processor 68 are one or more software modules which operate on the angle indication signal 56 to generate a joint angle signal (step 120). In the preferred embodiment, the software modules running on the processor 68 perform an envelope detection, or similar function, on the angle indication signal 56 to extract and properly scale the angle information in the joint angle signal.

Based on the joint angle signal, the display device 72, such as a video card and monitor, provides a visual image of variations in the joint angle value versus time (step 122). For example, the visual image may resemble a continuously running linear "strip chart" style display of joint angle. Alternatively, the visual display may take the form of two lines which intersect at an angle corresponding to the joint angle $\theta_J$, where the angle between the two lines changes with time according to the angle indication signal 56. Preferably, an elapsed time graphic is simultaneously provided on the display device 72, such as in a digital clock format.

In the preferred embodiment, the sound card 66 provides the audio annotation signal 62 to the speakers 74 in synchronicity with the display of joint angle $\theta_J$ on the display device 72, and the speakers 74 provide an audible rendition of the audio annotation signal 62 (step 124). This allows one to simultaneously observe the variations in joint angle $\theta_J$ and listen to the recorded voice annotations. In this manner, the system 10 correlates the joint angle information provided by the observed joint angle $\theta_J$ with concurrent physical activity as indicated by the voice annotations (step 126). For example, a golf coach or trainer may observe the joint angle $\theta_J$ of a student's elbow as the student makes a swing, and may correlate the start of the swing with the recorded voice of the student saying "Start." Of course, the microphone 60 may also pickup other sounds during the swing which provide valuable reference points for the observer, such as the sound of the club striking the ball.

Portable audio cassette tape recorders having stereo line inputs are readily available, fairly inexpensive, and simple to operate. Inexpensive audio tape cassettes are available which can hold up to two hours of audio information. Thus, the present invention provides an inexpensive and straightforward way to record hours of joint angle information and voice annotation information for later analysis. Further, since practically every personal computer currently on the market in practically every price range includes a sound card having a stereo line input, there is no need to provide a specially configured computer or other custom analysis device to analyze the joint angle information.

In the preferred embodiment of the invention, the signal 62 provides voice annotations related to the physical activity of the wearer. However, in other embodiments, the signal 62 may contain other biofeedback information. For example, the signal 62 could be a joint angle indication signal from a second angle sensing structure. Thus, it will be appreciated that the invention is not limited to any particular type of information provided by the signal 62.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A joint angle indication system for providing information related to an angular relationship between a first body part and a second body part which are pivotally coupled at a joint, the system comprising:
    a first arm member operable for attachment to the first body part, the first arm member having a first proximal end and a first distal end;
    a second arm member operable for attachment to the second body part, the second arm member having a second proximal end and a second distal end, the second proximal end of the second arm member pivotally coupled to the first proximal end of the first arm member;
    at least one joint angle variation sensor for providing at least one electrical characteristic which varies based on variation in a joint angle of the first arm member relative to the second arm member, where the joint angle is variable over an angular range which includes a first angle and a second angle, the at least one joint angle variation sensor comprising first and second potentiometers coupled between the first and second arm members for providing a first electrical resistance of the first potentiometer and a second electrical resistance of the second potentiometer;
    a biofeedback circuit operable to generate a first feedback signal when the first electrical resistance of the first potentiometer indicates the joint angle is less than or equal to the first angle, operable to generate the second feedback signal when the first electrical resistance of the first potentiometer indicates the joint angle is greater than or equal to the second angle, and operable to generate no feedback signal when the first electrical resistance of the first potentiometer indicates the joint angle is less than the second angle and greater than the first angle; and
    an angle display circuit for visually displaying a joint angle value based on at least the second electrical resistance.

2. The joint angle indication system of claim 1 wherein:
    the first arm member is forked at the first proximal end to form a first prong portion and a second prong portion;
    the second proximal end of the second arm member is disposed between the first and second prong portions of the first arm member;
    the first potentiometer is disposed between the second arm member and the first prong of the first arm member, and
    the second potentiometer is disposed between the second arm member and the second prong of the first arm member.

3. The joint angle indication system of claim 1 wherein the biofeedback circuit further comprises a first piezoelectric buzzer for generating the first feedback signal and a second piezoelectric buzzer for generating the second feedback signal.

4. The joint angle indication system of claim 1 further comprising an audio output circuit for generating an audio angle indication signal having a signal characteristic which varies in relation to a variation in the at least one electrical characteristic.

5. The joint angle indication system of claim 4 wherein the signal characteristic which varies in relation to a variation in the at least one electrical characteristic is the frequency of the audio angle indication signal.

6. The joint angle indication system of claim 5 further comprising a microphone for generating an audio annotation signal.

7. A joint angle indication system for providing information related to an angular relationship between a first body part and a second body part which are pivotally coupled at a joint, the system comprising:
    a first arm member operable for attachment to the first body part, the first arm member having a first proximal end and a first distal end;
    a second arm member operable for attachment to the second body part, the second arm member having a second proximal end and a second distal end, the second proximal end of the second arm member pivotally coupled to the first proximal end of the first arm member;
    at least one joint angle variation sensor for providing at least one electrical characteristic which varies based on variation in a joint angle of the first arm member relative to the second arm member, where the joint angle is variable over an angular range which includes a first angle and a second angle;
    a biofeedback circuit operable to generate a first feedback signal when the at least one electrical characteristic indicates the joint angle is less than or equal to the first angle, operable to is generate a second feedback signal when the at least one electrical characteristic indicates the joint angle is greater than or equal to the second angle, and operable to generate no feedback signal when the at least one electrical characteristic indicates the joint angle is less than the second angle and greater than the first angle, where the second feedback signal is aurally different from the first feedback signal;
    an angle display circuit for visually displaying a joint angle value based on the at least one electrical characteristic;
    a flexible sleeve operable to substantially surround the first and second body parts;
    the first arm member having a first attachment plate pivotally attached thereto proximate the first distal end;

means for mechanically coupling the first attachment plate to the flexible sleeve;

the second arm member having a second attachment plate pivotally attached thereto proximate the second distal end; and means for mechanically coupling the second attachment plate to the flexible sleeve.

8. The joint angle indication system of claim 7 wherein the means for mechanically coupling the first attachment plate to the flexible sleeve and the means for mechanically coupling the second attachment plate to the flexible sleeve further comprise a hook-and-loop fastener system.

9. The joint angle indication system of claim 7 wherein:

the means for mechanically coupling the first attachment plate to the flexible sleeve comprises at least one first pocket in the flexible sleeve for receiving the first attachment plate; and the means for mechanically coupling the second attachment plate to the flexible sleeve comprises at least one second pocket in the flexible sleeve for receiving the second attachment plate.

10. A joint angle indication system for providing information related to an angular relationship between a first body part and a second body part which are pivotally coupled at a joint, the system comprising:

a first arm member operable for attachment to the first body part, the first arm member having a first proximal end and a first distal end;

a second arm member operable for attachment to the second body part, the second arm member having a second proximal end and a second distal end, the second proximal end of the second arm member pivotally coupled to the first proximal end of the first arm member;

at least one joint angle variation sensor for providing at least one electrical characteristic which varies based on variation in a joint angle of the first arm member relative to the second arm member, where the joint angle is variable over an angular range which includes a first angle and a second angle, an audio output circuit for generating an audio angle indication signal having a frequency that varies in relation to a variation in the at least one electrical characteristic;

a biofeedback circuit operable to generate a first feedback signal when the at least one electrical characteristic indicates the joint angle is less than or equal to the first angle, operable to generate a second feedback signal when the at least one electrical characteristic indicates the joint angle is greater than or equal to the second angle, and operable to generate no feedback signal when the at least one electrical characteristic indicates the joint angle is less than the second angle and greater than the first angle, where the second feedback signal is aurally different from the first feedback signal;

an angle display circuit for visually displaying a joint angle value based on the at least one electrical characteristic;

a microphone for generating an audio annotation signal; and an audio recording device operable to record audio information on at least first and second audio information channels, the audio recording device for receiving the audio angle indication signal and recording the audio angle indication signal on the first audio information channel, and for receiving the audio annotation signal and recording the audio annotation signal on the second audio information channel.

11. A joint angle indication system for providing information related to an angular relationship between a first, body part and a second body part which are pivotally coupled at a joint, the system comprising:

a first arm member operable for attachment to the first body part, the first arm member having a first proximal end and a first distal end, the first arm member forked at the first proximal end to form a first prong portion and a second prong portion;

a second arm member operable for attachment to the second body part, the second arm member having a second proximal end and a second distal end, the second proximal end of the second arm member disposed between and pivotally coupled to the first and second prong portions of the first arm member;

a first potentiometer disposed between the second arm member and the first prong of the first arm member, the first potentiometer having a first electrical resistance which varies based on variation in a joint angle of the first arm member relative to the second arm member, where the joint angle is variable over an angular range which includes a first angle and a second angle;

a second potentiometer disposed between the second arm member and the second prong of the first arm member, the second potentiometer having a second electrical resistance which varies based on the variation in the joint angle;

a biofeedback circuit operable to generate a first feedback signal having a first audio frequency when the first electrical resistance indicates the joint angle is less than or equal to the first angle, operable to generate a second feedback signal having a second audio frequency which is higher than the first audio frequency when the first electrical resistance indicates the joint angle is greater than or equal to the second angle, and operable to generate no feedback signal when the first electrical resistance indicates the joint angle is less than the second angle and greater than the first angle; and an angle display circuit for visually displaying a joint angle value based on the second electrical resistance.

12. A joint angle indication system for providing information related to an angular relationship between a first body part and a second body part which are pivotally coupled at a joint, the system comprising:

a first arm member operable for attachment to the first body part, the first arm member having a first proximal end and a first distal end;

a second arm member operable for attachment to the second body part, the second arm member having a second proximal end and a second distal end, the second proximal end of the second arm member pivotally coupled to the first proximal end of the first arm member;

at least one joint angle variation sensor for providing at least one electrical characteristic which varies based on variation in a joint angle of the first arm member relative to the second arm member, where the joint angle is variable over an angular range which includes a first angle and a second angle;

a biofeedback circuit operable to generate a first feedback signal when the at least one electrical characteristic indicates the joint angle is less than or equal to the first angle, operable to generate a second feedback signal when the at least one electrical characteristic indicates the joint angle is greater than or equal to the second angle, and operable to generate no feedback signal when the at least one electrical characteristic indicates the joint angle is less than the second angle and greater than the first angle, where the second feedback signal is aurally different from the first feedback signal;

an audio output circuit for generating an audio angle indication signal having a frequency which varies in relation to a variation in the at least one electrical characteristic;

a microphone for generating an audio annotation signal; and an audio recording device operable to record audio information on at least first and second audio information channels, the audio recording device for receiving and recording the audio angle indication signal on the first audio information channel, and for receiving and recording the audio annotation signal on the second audio information channel.

13. A method for providing information related to an angular relationship between a first body part and a second body part which are pivotally coupled at a joint, the method comprising:
   (a) providing at least one electrical characteristic which varies based on variation in a joint angle of the first body part relative to the second body part, where the joint angle is variable over an angular range which includes a first angle and a second angle;
   (b) generating an audio angle indication signal having a signal characteristic which varies in relation to a variation in the at least one electrical characteristic;
   (c) generating an audio annotation signal;
   (d) recording the audio angle indication signal on a first audio information channel of an audio recording device, and recording the audio annotation signal on a second audio information channel of the audio recording device;
   (e) accessing the audio angle indication signal from the first audio information channel of the audio recording device, and accessing the audio annotation signal from the second audio information channel of the audio recording device;
   (f) operating on the audio angle indication signal to derive a joint angle signal therefrom;
   (g) displaying a joint angle value on a display device based on the joint angle signal; and
   (h) providing an audible rendition of the audio annotation signal.

14. The method of claim 13 further comprising temporally correlating the joint angle value displayed in step (g) with the audible rendition of the audio annotation signal provided in step (h).

15. The method of claim 13 further comprising:
   (i) generating a first feedback signal when the at least one electrical characteristic indicates the joint angle is less than or equal to the first angle; and
   (j) generating a second feedback signal when the at least one electrical characteristic indicates the joint angle is greater than or equal to the second angle, the second feedback signal having a frequency higher than the first feedback signal.

16. The method of claim 13 wherein:
   step (d) further comprises recording the audio angle indication signal on a first audio information channel of a portable cassette tape recorder, and recording the audio annotation signal on a second audio information channel of the portable cassette tape recorder; and
   step (e) further comprises providing the first and second audio information channels of the portable cassette tape recorder to first and second channel inputs of a computer sound card.

17. A joint angle indication system for providing information related to an angular relationship between a first body part and a second body part which are pivotally coupled at a joint, the system comprising:
   a first arm member operable for attachment to the first body part, the first arm member having a first proximal end and a first distal end, the first arm member forked at the first proximal end to form a first prong portion and a second prong portion;
   a second arm member operable for attachment to the second body part, the second arm member having a second proximal end and a second distal end, the second proximal end of the second arm member disposed between and pivotally coupled to the first and second prong portions of the first arm member;
   a first potentiometer disposed between the second arm member and the first prong of the first arm member, the first potentiometer having a first electrical resistance which varies based on variation in a joint angle of the first arm member relative to the second arm member, where the joint angle is variable over an angular range which includes a first angle and a second angle; and
   a second potentiometer disposed between the second arm member and the second prong of the first arm member, the second potentiometer having a second electrical resistance which varies based on the variation in the joint angle.

18. The joint angle indication system of claim 17 further comprising a biofeedback circuit operable to generate a feedback signal based on at least the first electrical resistance.

19. The joint angle indication system of claim 17 further comprising an angle display circuit for visually displaying a joint angle value based on at least the second electrical resistance.

20. A joint angle indication system for providing information related to an angular relationship between a first body part and a second body part which are pivotally coupled at a joint, the system comprising:
   a first arm member operable for attachment to the first body part, the first arm member having a first proximal end and a first distal end;
   a second arm member operable for attachment to the second body part, the second arm member having a second proximal end and a second distal end, the second proximal end of the second arm member pivotally coupled to the first proximal end of the first arm member;
   at least one joint angle variation sensor for providing at least one electrical characteristic which varies based on variation in a joint angle of the first arm member relative to the second arm member, where the joint angle is variable over an angular range which includes a first angle and a second angle;
   a biofeedback circuit operable to generate a first feedback signal when the at least one electrical characteristic indicates the joint angle is less than or equal to the first angle, operable to generate a second feedback signal when the at least one electrical characteristic indicates the joint angle is greater than or equal to the second angle, and operable to generate no feedback signal when the at least one electrical characteristic indicates the joint angle is less than the second angle and greater than the first angle, where the second feedback signal is aurally different from the first feedback signal;

an audio output circuit for generating an audio angle indication signal having a frequency which varies in relation to a variation in the at least one electrical characteristic; and an audio recording device operable to receive and record the audio angle indication signal.

21. The joint angle indication system of claim 20 further comprising:

a microphone for generating an audio annotation signal; and the audio recording device operable to record audio information on at least first and second audio information channels, the audio recording device for receiving and recording the audio angle indication signal on the first audio information channel, and for receiving and recording the audio annotation signal on the second audio information channel.

22. A method for providing information related to an angular relationship between a first body part and a second body part which are pivotally coupled at a joint, the method comprising:

(a) providing at least one electrical characteristic which varies based on variation in a joint angle of the first body part relative to the second body part, where the joint angle is variable over an angular range which includes a first angle and a second angle;

(b) generating an audio angle indication signal having a signal characteristic which varies in relation to a variation in the at least one electrical characteristic;

(c) recording the audio angle indication signal on a first audio information channel of an audio recording device;

(d) accessing the audio angle indication signal from the first audio information channel of the audio recording device; and (e) operating on the audio angle indication signal to derive a joint angle signal there from.

23. The method of claim 22 further comprising displaying a joint angle value on a display device based on the joint angle signal.

24. The method of claim 22 further comprising:

(f) generating an audio annotation signal;

(g) recording the audio annotation signal on a second audio information channel of the audio recording device;

(h) accessing the audio annotation signal from the second audio information channel of the audio recording device; and (i) providing an audible rendition of the audio annotation signal.

* * * * *